United States Patent [19]

Schouenborg

[11] Patent Number: 5,449,378
[45] Date of Patent: Sep. 12, 1995

[54] METHOD AND APPARATUS FOR THE ELECTRIC STIMULATION OF SKIN RECEPTORS

[76] Inventor: Jens Schouenborg, Rudeboksvägen 397, SE-226 55 Lund, Sweden

[21] Appl. No.: 170,338
[22] PCT Filed: Apr. 5, 1993
[86] PCT No.: PCT/SE93/00287
§ 371 Date: Dec. 30, 1993
§ 102(e) Date: Dec. 30, 1993
[87] PCT Pub. No.: WO93/23112
PCT Pub. Date: Nov. 25, 1993

[30] Foreign Application Priority Data

May 8, 1992 [SE] Sweden ............... 9201453

[51] Int. Cl.[6] ............................. A61N 1/04
[52] U.S. Cl. .................. 607/46; 607/115; 607/148; 607/152
[58] Field of Search ........... 607/2, 46, 48, 50, 115, 607/148, 152, 1; 128/639

[56] References Cited

U.S. PATENT DOCUMENTS

| | | |
|---|---|---|
| 3,612,061 | 10/1971 | Collins et al. |
| 4,254,776 | 3/1981 | Tanie et al. |
| 4,453,548 | 6/1984 | Maurer et al. |
| 4,509,535 | 4/1985 | Bryan |
| 4,685,466 | 8/1987 | Rau |
| 4,708,149 | 11/1987 | Axelgaard et al. |
| 4,722,354 | 2/1988 | Axelgaard et al. |
| 4,823,810 | 4/1989 | Dervieux |
| 4,837,049 | 6/1989 | Byers et al. ............ 607/115 |
| 4,867,166 | 9/1989 | Axelgaard et al. |
| 4,920,968 | 5/1990 | Takase ............ 607/123 |
| 4,926,879 | 5/1990 | Sevrain et al. |
| 4,982,742 | 1/1991 | Claude |
| 4,982,743 | 1/1991 | Pierson |
| 5,038,796 | 8/1991 | Axelgaard et al. |
| 5,058,605 | 10/1991 | Slovak |
| 5,067,495 | 11/1991 | Brehm |
| 5,133,354 | 7/1992 | Kallok ............ 607/48 |
| 5,178,161 | 1/1993 | Kovacs ............ 607/115 |

FOREIGN PATENT DOCUMENTS

| | | |
|---|---|---|
| 0249532 | 12/1987 | European Pat. Off. |
| 0268701 | 6/1988 | European Pat. Off. |
| 0377057 | 7/1990 | European Pat. Off. |
| 2555281 | 6/1977 | Germany |
| 3236756 | 4/1984 | Germany |
| 4000893 | 7/1991 | Germany |
| WO90705560 | 5/1990 | WIPO |
| WO91/06340 | 5/1991 | WIPO |

OTHER PUBLICATIONS

Information Sheet, Trimix 101H, Nihon Medix Co., Ltd.
Information Sheet, Phyaction 912, Uniphy B.V.

*Primary Examiner*—William E. Kamm
*Assistant Examiner*—Kennedy J. Schaetzle
*Attorney, Agent, or Firm*—Burns, Doane, Swecker & Mathis

[57] ABSTRACT

A device for relieving chronic and acute states of pain as well as itch, for affecting the motor activity of disabled people, or for increasing the flow-through of blood in underlying tissue, includes a shapable electrode plate (1) through which extend a plurality of electrodes (2) fixed in the electrode plate (1) and terminating, at their respective free ends, in electrode tip portions (7) for skin penetration. The electrode tip portion (7) of each electrode (2), at a distance of about 0.1–2.0 mm from the electrode tip (8), is surrounded by stop means (9) separating the electrode plate (1) from the skin portion (10). The electrodes (2) cooperate with a collector electrode (6) of opposite electrical polarity to the electrodes (2), and the electrodes (2) and the collector electrode (6) are electrically connected to a control unit (4) designed to activate the electrodes (2) consecutively, so that when pressure is applied on the electrodes (2), the electrode tip portions (7) will penetrate the isolating outer layers of the epidermis to stimulate the receptors of the skin.

24 Claims, 2 Drawing Sheets

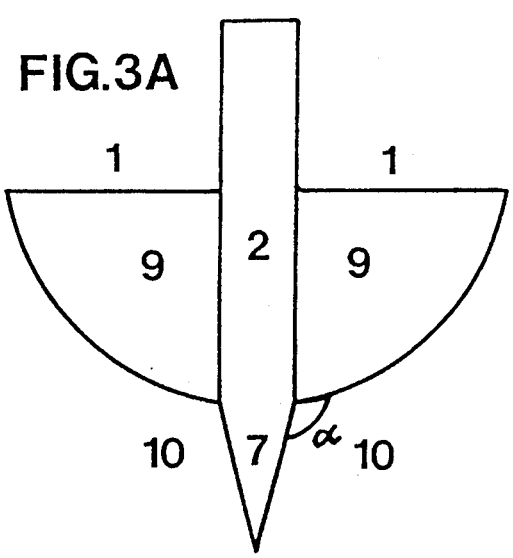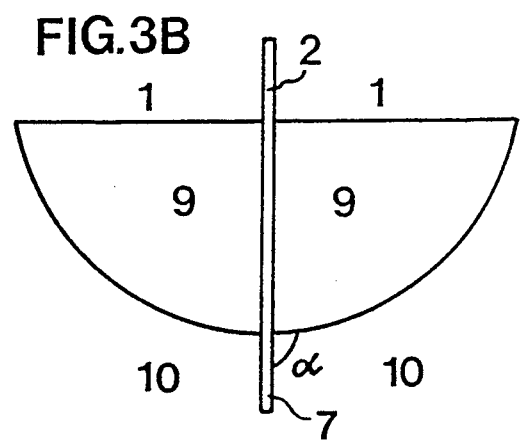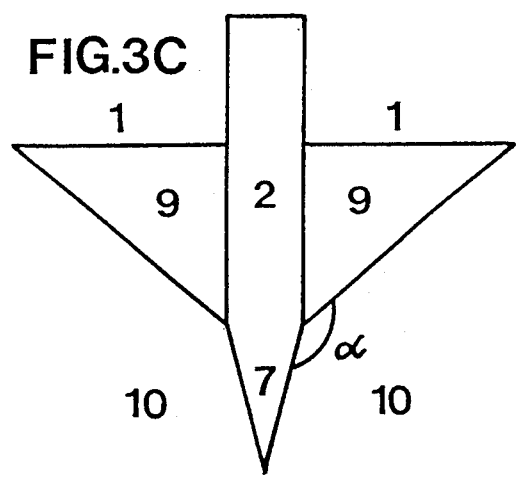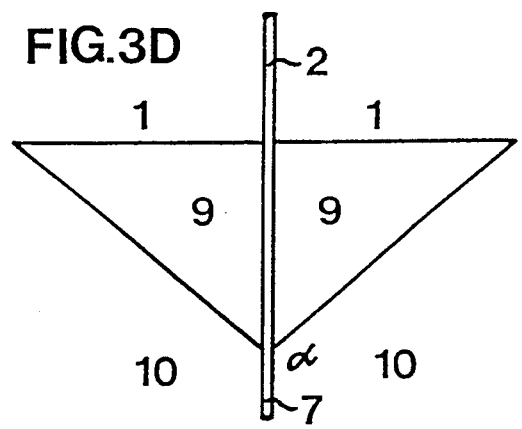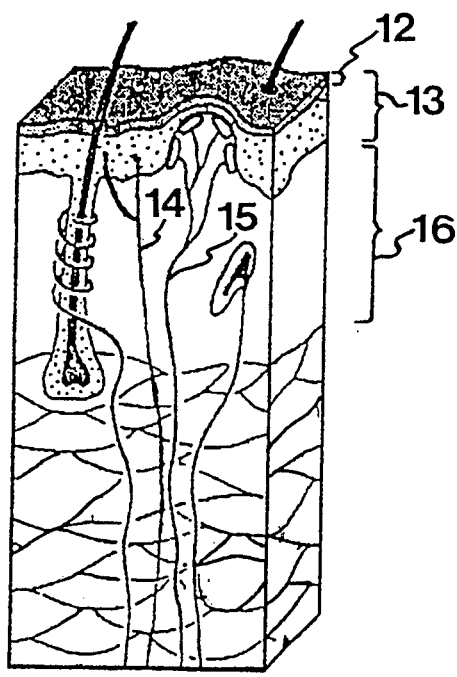

METHOD AND APPARATUS FOR THE ELECTRIC STIMULATION OF SKIN RECEPTORS

The present invention relates to a device and a method for relieving chronic and acute states of pain as well as itch, for affecting the motor activity of disabled people, or for increasing the flow-through of blood in underlying tissue. The device comprises a shapable electrode plate through which extend a plurality of electrodes which are fixed in the electrode plate and terminate, at their respective free ends, in an electrode tip portion for skin penetration. The invention also concerns the use of the device for relieving chronic and acute states of pain as well as itch, for affecting the motor activity of disabled people, or for increasing the flow-through of blood in underlying tissue.

It is well-known that the activation of sensitive mechanoreceptors in the skin may relieve pain as well as itch, and quite a number of theories trying to explain the underlying mechanisms have been launched in the past 25 years. The most well-known theory, the gate theory (Melzack and Wall, Science, 150:971–979, 1965), describes in great detail how the interaction between mechanoreception and pain might work. On the basis of this theory, apparatus for transcutaneous electrical nerve stimulation (TENS) were developed in the 70s and 80s to provide pain relief. These apparatus activate whole nerves (nerve fibre bands) from the skin and the underlying tissue. By using a suitable current intensity, thick myelinated nerve fibres from sensitive mechanoreceptors can be preferentially stimulated, having the lowest threshold for electrical stimulation. This method has been found to have analgetic effects for some states of pain in about 50% of the patients tested.

The majority of nociceptors (injury receptors) have slowly transferring non-myelinated axons, so-called C fibres. These are believed to play a crucial part in chronic states of pain. Previously, one was labouring under the misapprehension that the pain paths activated by these fibres have a diffuse topographic organisation. However, more recent neurophysiological studies have shown that the pain paths have a very detailed organisation with well-defined activating and inhibiting skin areas (Schouenborg, J. Physiol, 356:169–192, 1984; Schouenborg and Kalliomäki, Exp. Brain Res. 83:67–78, 1990). If effective pain relief is to be achieved, local inhibitory skin areas should thus be specifically stimulated. Established TENS technique does not provide this possibility, since whole nerves from the skin as well as the underlying tissue are stimulated. In addition, the different peripheral nerves practically never supply functionally defined areas.

Studies of the organisation of the pain paths have shown that pain-activated nerve cells, as well as other nerve cells receiving information from the body surface, can be maximally activated from very small areas of the skin. Consequently, it is unnecessary, and probably wrong, to stimulate whole nerves supplying large receptor beds. By consecutively stimulating different nearby points at a low frequency for each point, one might obtain high-frequency activation of central nerve cells without tiring individual inward-leading nerve fibres and central synapses.

The knowledge of central nerve paths mediating itch is quite limited. Itch makes one want to scratch the skin, providing a certain relief. Regrettably, scratching often worsens the itch in the long run by injuring the tissue. Thus, it is desirable to activate the central itch-relieving mechanisms without injuring the skin.

Recent research has also revealed that individual muscles can be activated and inhibited from specific skin areas. The areas activating a given muscle correspond to those areas of the skin that the muscle removes upon contraction, and the areas inhibiting a given muscle correspond to those areas of the skin that are moved by the muscle towards a stationary object upon contraction. Muscular activity might be controlled by specifically activating these areas of the skin. This is of importance in order to facilitate motor activity or alter involuntary motor activity under various disabling conditions.

The object of the present invention is to provide a device and a method enabling specific stimulation of the receptors in the skin in order to relieve chronic and acute states of pain as well as itch, affect the motor activity of disabled people, or increase the flow-through of blood in underlying tissue.

This object is achieved by a device and a method which are of the type indicated by way of introduction and which in addition exhibit the features recited in the characterising clauses of the appended claims. Preferred embodiments of the invention are defined in the subclaims.

The inventive device differs from existing TENS apparatus by the stimulation being performed locally within a defined and functional area of the skin, TENS stimulating whole nerves which convey unspecific information from the skin as well as the underlying tissue. Since stimulation from multiple points can be performed consecutively, thus reaching individual skin receptors at a relatively low frequency, fatigue phenomena (accommodation) of individual inward-leading nerve fibres and their central synapses can be reduced. TENS, on the other hand, activate whole nerves, and consequently a large number of nerve fibres, which involves a pronounced fatigue phenomenon.

Furthermore, TENS generates an unpleasant sensation of current owing to the synchronous activation of nerve fibres. This sensation often radiates along the distribution of the stimulated nerves.

The inventive device, on the other hand, initially gives rise to a local and brief pricking pain which largely can be eliminated by gradually increasing the intensity of the stimulation. In addition, the inventive device makes it possible to use a lower current intensity (6 mA at the most) than in TENS (30–60 mA). The voltage used in the invention (40 V at the most, usually below 20 V) is also much lower than that used in TENS (50–200 V). This reduces the risk of complications, e.g. for people with pacemakers.

Moreover, the present invention differs from acupuncture in the following way. In acupuncture, the skin is punctured by individual needles which penetrate the underlying tissue. Stimulation is brought about either by electrical current or by mechanical manipulation. Since the needles used are not insulated, current dissipates along the needles, resulting in an unspecific stimulation of receptors in the skin as well as deeper-lying tissue. Often, acupuncture also activates nearby nerves passing by. Thus, acupuncture differs from the present invention primarily by providing unspecific stimulation of different types of receptors along the needle and nearby nerves. Furthermore, the current intensity used in acupuncture is, as a rule, higher than that used in the invention.

U.S. Pat. No. 3,612,061 (Collins et al) relates to a flexible electrode matrix. The aim of this invention is to use the tactile sense of blind people for transmitting information. The US device consists of a flexible sheet or plate with electrodes placed in a matrix. Each electrode is connected to a separate, lying cable to a power supply unit. The sheet is earthed. The electrodes can be individually stimulated, and the electrode matrix may therefore be stimulated according to different patterns. Each electrode projects from the sheet and consists of a cylinder having a convex surface which is applied to the skin under pressure. Among other things, the US device differs from the present invention in that the electrodes do not penetrate the skin. No parameters for the stimulation are indicated. However, the electrodes are apparently not intended to be stimulated consecutively, a spatial pattern being aimed at. Since the electrodes do not penetrate the skin, a higher voltage is needed for stimulating the skin receptors/nerves. As a result, the current dissipates to a larger extent and is less specific than in the present invention.

U.S. Pat. No. 4,982,743 (Pierson) relates to an itch reducer, which comprises an electrode sheet or plate (smaller than 4 $cm^2$) having projecting and blunt electrodes to be applied against the skin. The electrodes project 0.2–1.0 mm from the sheet. However, the electrode tips are not pointed and are only pressed slightly into the skin when the electrode head is applied against the skin surface. The U.S. specification explicitly states that the electrodes do not penetrate or perforate the skin. The skin is stimulated by direct voltage (20 V at the most) for up to a minute or so. It is further indicated that the stimulation is not felt (i.e. does not noticeably activate the skin receptors) while the itch is relieved. The US itch reducer differs from the present invention in that the electrodes, as already stated, are not designed to penetrate the skin. Furthermore, direct current is used, and not pulsed stimulation. Unlike the inventive device, the US device does not provide any possibility of consecutively stimulating the different projecting electrodes. Finally, the size of the sheet is even smaller than 4 $cm^2$.

EP-A-0,377,057 (Bernardini et al) relates to a hand-operated electromedical device for analgetic skin treatment, more precisely a portable apparatus having four electrode pairs embedded in a plate. The electrodes, which are blunt and shown as round in the accompanying drawing, do not penetrate the skin. The electrode pairs are stimulated at the same frequency. Any parameters for the stimulation are not indicated, neither are the dimensions of the apparatus. The EP apparatus differs from the inventive device in that the electrodes do not penetrate the skin and in that only a few electrode pairs are used. Further, it is not possible to stimulate these electrodes consecutively. The stimulation voltage should, in addition, be much higher in order to activate receptors/nerves, as in conventional TENS. Moreover, the current density does not become as high intracutaneously.

The state of the art is further disclosed in EP-A0,249,532 (Ory), U.S. Pat. No. 4,982,742 (Claude), U.S. Pat. No. 4,509,535 (Bryan), U.S. Pat. No. 4,453,548 (Maurer et al) and U.S. Pat. No. 4,823,810 (Dervieux), as well as U.S. Pat. Nos. 4,708,149, 4,722,354, 4,867,166 and 5,038,796 (all to Axelgaard and Grussing). The devices taught by these publications all have in common that no penetration of the skin by electrodes takes place, and the mechanoreceptors and pain receptors of the skin can therefore not be specifically stimulated. Furthermore, none of these devices enables consecutive stimulation.

BRIEF DESCRIPTION OF THE DRAWING FIGURES

The invention will be described in more detail below with reference to the accompanying drawings, in which FIG. 1 is a side view of a preferred embodiment of the inventive device;

FIG. 3 is a section of four different embodiments of the electrode tip portion and the stop means according to the invention; and FIG. 4 is a section in perspective of a skin portion.

DETAILED DESCRIPTION

Figure 1:
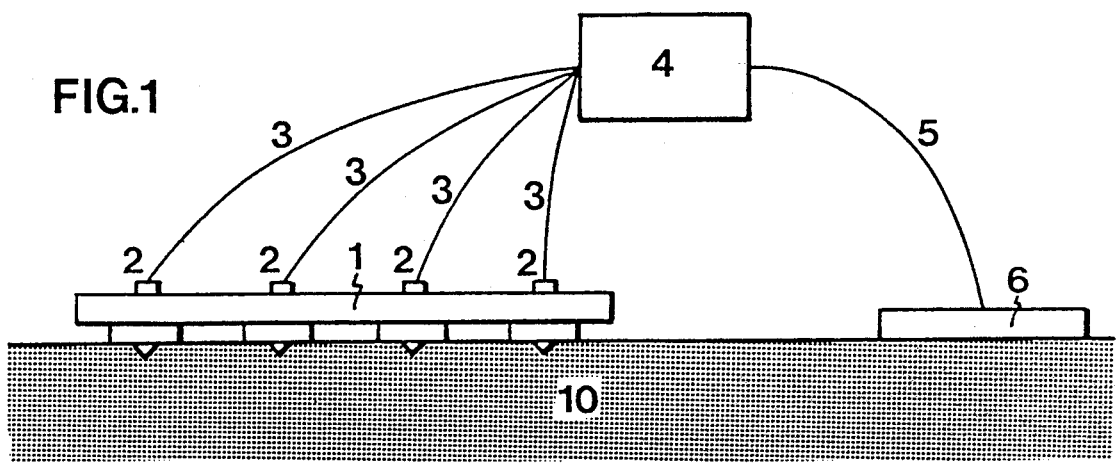

As appears from FIG. 1, an electrode plate 1 is provided with several electrodes 2 fixed in the plate 1 and extending therethrough. Each electrode 2 is connected to a control unit 4 by an electric line 3. The control unit 4 is in turn connected, by an electric line 5, to a collector electrode 6 of opposite electrical polarity to the electrodes 2. The electrode plate 1 with the electrodes 2 projecting from its underside, and the collector electrode 6 are applied to a skin portion 10 during the stimulation operation.

Preferably, the electrode plate 1 is shapable and substantially flat. The plate may be of different size, depending on the size of the skin portion to be stimulated. Further, the plate is made of some conventional pliable material enabling it to be used on curved parts of the body, such as the elbows, the shoulders and the knees. The plate may be about 1–500 $cm^2$, but preferably is about 4–300 $cm^2$.

Naturally, the size of the plate depends on the skin area to be stimulated. Where the skin has low receptor density, fairly large areas have to be stimulated. For instance, comparatively large areas are stimulated on the back and the back of the head, while smaller areas are stimulated on the arms and the face. If need be, one or more electrode plates 1 may in addition be connected when large areas of the skin are to be stimulated. Electrically, the electrode plate 1 may be an insulator in its entirety or it may be made up of an insulator in the layer closest to the skin and, in an overlying layer, consist either of electrically conductive wires from the electrodes 2 to the control unit 4 or of printed board. In a preferred embodiment, the electrode plate 1 is a sleeve of silicon rubber.

Figure 2:
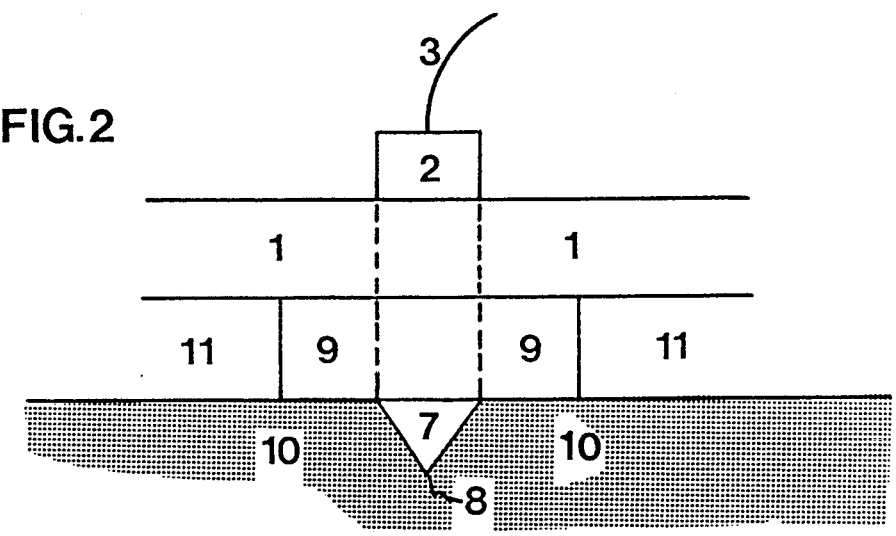
FIG. 2 is a section of an electrode arranged in the electrode plate of the device shown in FIG. 1.

Electrodes 2 extend through recesses in the electrode plate 1 and project from the underside of the plate facing the skin portion 10, as shown in FIG. 2. The electrodes 2 are substantially elongate and are made of conventional conductive material. By an electric line 3, the upper end of each electrode 2 is connected to the control unit 4. This upper end may project from the upper side of the electrode plate 1 facing away from the skin portion or it may be embedded in the electrode plate 1. At the lower end, the electrode 2 ends in an electrode tip portion 7 intended to penetrate the skin portion 10. It is of considerable importance that the electrode tip portion 7 is so designed that it can penetrate the skin sufficiently to achieve the desired stimulation of the skin receptors. The electrode tip portion 7 is pointed at an angle less than 90°, preferably less than 45°. The electrode tip portion 7 may be perfectly conically pointed or convexly/concavely conically pointed or it may have a cutting edge. It may also be otherwise designed, provided that it meets the requirements at issue, and thus may have the shape of a needle or a pin. The cross-sectional surface of the electrode tip portion 7 can also be so small that The skin is penetrated under the exertion of a pressure, regardless of its design. The cross-sectional surface should be about 1 mm$^2$ at the most, preferably 0.25 mm$^2$ at the most, in order to minimise skin injuries caused by the penetration.

To achieve controlled penetration, a stop means 9 is furthermore provided round the projecting lower electrode part formed with the electrode tip portion 7, in such a manner that it also surrounds the electrode 2 and serves as a spacer between the underside of the electrode plate 1 and the skin portion 10. This also creates an air gap 11 between the electrode plate 1 and the skin portion 10. The term "electrode tip portion" is used to designate the portion of the electrode 2 projecting from the stop means 9. The stop means 9 can be made of any conventional material, e.g. either an electrically conductive material or an insulating material, and have any suitable design. Preferably, the stop means is a hollow cylinder with a height of about 0.1–5 mm. Its skin contact surface, which preferably is annular, has a size of about 0.2–25 mm$^2$, depending on the electrode density and the curvature of the skin surface. In a preferred embodiment, the skin contact surface of the stop means 9 is about 3 mm$^2$. The stop means 9 may be a separate component of the device, but it may also be made in one piece with the electrodes 2. Thus, the stop means 9 enables the electrode 2 to penetrate to a predetermined depth in the skin when pressure is applied from above. Preferably, the lower end of the stop means 9 is convex for optimal skin contact. The skin contact surface may alternatively be flat, be flat closest to the electrode tip portion 7 and rounded up towards the electrode plate 1, or be conical. As appears from FIGS. 3A–D, showing alternative embodiments of the invention, the angle $\alpha$ between the stop means 9 and the electrode tip portion 7 should not exceed 160° to enable satisfactory control of the penetration depth of the electrode 2 into the skin. In the preferred embodiment, the angle $\alpha$ between the stop means 9 and the electrode tip portion 7 is about 90°. Basically, a device in which the electrode plate 1 in itself serves as stop means is also conceivable. However, such an arrangement does not enable satisfactory control of the penetration depth of the electrodes 2 into the skin.

Since different receptors are located at different depths in the skin, it is possible to select the group of receptors to be stimulated by varying the penetration depth of the electrode tip portion 7 into the skin. The present invention is preferably used for stimulating receptors in the lower part of the epidermis and the upper part of the dermis. When the electrode 2 is applied to the skin portion 10 under the exertion of a pressure, the electrode tip portion 7 perforates the electrically insulating layers of the epidermis (stratum corneum and stratum lucidum, i.e. the horny layer made up of dead cells of the skin. As appears from FIG. 4, which is a section illustrating the structures and the positions of receptors in the skin, the electrodes 2 should reach down to the lower part of the epidermis 13 and the upper part of the dermis 16, being the location of both nociceptors 14 and sensitive mechano-receptors 15. The term "receptors" used throughout this description relates to mechanoreceptors and nociceptors as well as their intracutaneous nerve fibres in the layers of the skin 13 and 16. The horny layer 12 constitutes the uppermost part of the epidermis 13. When the electrode tip portion 7 passes these layers of the skin, the electrical resistance between the electrode tip and the receptor is considerably reduced. The voltage and the current intensity required for activating receptors in the skin may therefore be considerably reduced as well. The skin penetration depth, i.e. the vertical distance between the tip 8 of the electrode tip portion 7 and an imaginary extension of the surface of the stop means 9 applied against the skin portion 10, depends on the type of skin to be stimulated and on how far into the skin stimulation is to take place. The electrode tip portion 7 preferably projects about 0.1–2.0 mm, in a particularly preferred embodiment about 0.2–1.2 mm. The term "skin penetration", used throughout the description and the claims, encompasses penetration through the skin layers to the sensitive mechanoreceptors 15 and the nociceptors 14 found in the lower part of the epidermis 13 and the upper part of the dermis 16.

The electrodes 2 can be arranged at different distances from the electrode plate 1. For practical reasons, however, distances above about 30–50 mm and below about 2–5 mm should not be used. The number of electrodes 2 per electrode plate 1 may vary between about 2 and 100, and preferably is about 15–50. However, an electrode plate 1 having but a single electrode might also be used. In that case, pain relief would be more limited than when using the preferred embodiment with multiple electrodes. The electrodes 2 can be asymmetrically arranged on the electrode plate 1, depending on the skin portion to be treated. The above parameters are easily determined by anyone skilled in the art.

In a preferred embodiment of the invention, the plate is oval or rectangular and has a surface area of about 100 cm$^2$, 16 electrodes being symmetrically arranged on the plate and spaced apart 20 mm. In the preferred embodiment, the electrodes 2 are in addition cylindrical and have a diameter of about 0.5 mm.

In the preferred embodiment, the electrode plate 1 consists of an upper layer having integrated lines/-printed boards and a lower insulator layer. The stop means 9 is made in one piece with the electrodes 2.

The control unit 4, which is connected to each electrode 2 on the electrode plate 1 by electric lines 3, utilises conventional electronics and is designed to provide the required values of the electronic parameters used in the invention. The control unit 4 may be either enclosed in a separate container or encased directly on the electrode plate 1. In the preferred embodiment of the invention, the electrodes are activated consecutively, i.e. in turn, to achieve optimal effect. Although simultaneous stimulation of all the electrodes is possible, this does not yield as good results. With the aid of the control unit 4, the frequency for each electrode 2 can be varied between about 1 Hz and 300 Hz, preferably between about 5 Hz and 100 Hz, but is about 40 Hz in a preferred embodiment. The voltage and the current intensity required for activating the receptors in the skin can, according to the invention, be reduced to about 40 V and about 6 mA, at the most, preferably to about 20 V and about 3 mA, at the most. In the preferred embodiment, the voltage does not exceed about 15 V and the current intensity does not exceed about 1–3 mA. When using the inventive device for pain and itch relief, the voltage is gradually increased during a first period lasting about 5–10 min, which considerably reduces any feeling of discomfort as compared with the discomfort felt when the stimulation voltage is increased stepwise to the required level. Stimulation then continues for about 20-50 min, but more time may be needed for some states of pain. The required pulse duration is about 0.01-5 ms, preferably 0.2-1 ms, and is 0.2 ms in a preferred embodiment. The above parameters depend on which portion of the skin is to be stimulated.

By an electric line 5, the control unit 4 is connected to a shapable, electrically conductive collector electrode 6, which is an electrode of opposite polarity to the electrodes 2. The collector electrode 6 is made of conventional material and may, like the electrode plate 1, be adjusted to curved body surfaces when need be. The shape and surface of the collector electrode 6 can be varied to a considerable extent, and the surface area is about 15-25 cm$^2$ in a preferred embodiment. When using the inventive device, the required current transfer takes place between the electrodes 2 and the collector electrode 6 of opposite polarity. The collector electrode 6 can be applied to the skin portion 10 at a distance from the electrode plate 1 or be applied as a frame round the plate. The collector electrode 6 may also be otherwise positioned in relation to the electrode plate 1.

Thus, the electrodes 2 can be either cathodes or anodes. When the electrodes 2 are cathodes, the collector electrode 6 is an anode, and vice versa. In a preferred embodiment of the invention, the electrodes 2 are cathodes and the collector electrode 6 is an anode.

In another embodiment of the invention, the electrodes 2 on the electrode plate 1 can operate in pairs as cathode and anode. Alternatively, groups of two or more electrodes 2 on the electrode plate 1 can act as mutual cathode-anode pairs with another group of electrodes 2 on the electrode plate 1. In this embodiment, the collector electrode 6 is superfluous and thus dispensed with.

The inventive device can be applied to The skin portion 10 at issue with the aid of a conventional fixing device (not shown), such as a sleeve with an adjustable clamping means, or with The aid of tissue adhesive. It is of great importance that the electrode plate 1 with the electrodes 2 and their electrode tip portions 7 can be applied against the skin portion at issue by adjustable pressure exertion to achieve the skin penetration required.

The present invention further concerns a method for relieving chronic and acute states of pain as well as itch, for affecting the motor activity of disabled people, or for increasing the flow-through of blood in underlying tissue, in which method a) a device according To The invention is applied with pressure against the skin portion to be stimulated, the electrode tip portions 7 of the electrodes 2 penetrating the skin portion 10 and reaching the area of the receptors; and b) the electrodes 2 are activated consecutively by the control unit 4 at a frequency of about 1-300 Hz, a current intensity not exceeding about 6 mA and a pulse duration of about 0.01-5 ms for a stimulation period of up to about 1 h.

The present invention also relates to the use of the inventive device for relieving chronic and acute states of pain as well as itch, for affecting the motor activity of disabled people, or for increasing the flow-through of blood in underlying tissue. The inventive device may also be used for more than one of these applications at the same time.

With the aid of the invention, it is thus possible to affect also the motor activity of disabled people whose muscles are partly or totally paralysed. Normally, the current intensity then is not gradually increased for 5-10 min. In such an instance, the skin area is stimulated in a manner coordinated with the intended motor activity.

Furthermore, the flow-through of blood in underlying tissue can be locally increased by stimulation with the aid of the device according to the invention. Such an increase in the blood flow has been shown, inter alia by an increase in temperature in the treated area of the skin.

Evaluation of the Analgetic and Itch-relieving Effects of the Invention

In a test involving 6 patients, pronounced and local pain relief in the stimulation area occurred within 3-5 min. The pain caused by heat stimulation of the skin surface showed that the pain threshold had been considerably raised. As a rule, the feeling of pin pricking disappeared completely. Moreover, tests on 4 patients with back muscle pain and tennis elbow showed good and long-term pain relief lasting several days.

In addition, the inventive device totally blocked itch, caused by an injection of histamine, in 3 patients and considerably relieved the itch in another 3 patients after about 5 min. of stimulation. The effect lasted more than 1 h.

What is claimed is:

1. A device for relieving chronic and acute states of pain as well as itch, for affecting the motor activity of disabled people, or for increasing the flow-through of blood in underlying tissue, said device comprising:
    a shapeable electrode plate;
    a plurality of electrodes which are fixed in the electrode plate and extend through the plate, the electrodes terminating, at respective free ends, in electrode tip portions for skin penetration;
    stop means surrounding the electrode tip portion of each electrode at a distance of about 0.1-2.0 mm from the electrode tip, the stop means separating the electrode plate from a skin portion; and
    the electrodes are electrically connected to a control unit designed to activate the electrodes consecutively, so that when pressure is applied on the electrodes the electrode tip portions will penetrate the isolating outer layers of the epidermis to stimulate the receptors of the skin.

2. A device as claimed in claim 1, wherein the control unit is designed to activate the electrodes consecutively at a frequency of about 1-300 Hz, a current intensity not exceeding about 6 mA, and a pulse duration of about 0.01-5 ms.

3. A device as claimed in claim 2, wherein the control unit is designed to activate the electrodes consecutively at a frequency of about 5-100 hz, a current intensity not exceeding about 3 mA, and a pulse duration of about 0.2-1.0 ms.

4. A device as claimed in claim 3, wherein the electrode plate has a surface area of 4-300 cm$^2$, and that 2-100 electrodes are fixed in the electrode plate.

5. A device as claimed in claim 2, wherein the electrode plate has a surface area of 4-300 cm$^2$, and that 2-100 electrodes are fixed in the electrode plate.

6. A device as claimed in claim 1, wherein the electrode plate has a surface area of 4-300 cm$^2$, and 2-100 electrodes are fixed in the electrode plate.

7. A device as claimed in claim 1, wherein the electrode tip portion of each electrode is pointed, being formed with one of a cutting edge or so small a cross-sectional surface that the skin portion is penetrated, regardless of the design of the electrode tip, and that the electrode tip portion is surrounded by the stop means at a distance of about 0.2–1.2 mm from the tip.

8. A device as claimed in claim 1, the stop means has a contact surface for contact with the skin that is flat closest to the electrode tip portion and rounded up toward the electrode plate.

9. A device as claimed in claim 1, comprising at least two electrode plates connected for stimulating a major skin portion.

10. A device as claimed in claim 1, wherein the electrodes in the electrode plate, in pairs or groups, form mutual anode-cathode pairs.

11. A device as claimed in claim 1, further comprising a collector electrode having opposite electrical polarity than an electrical polarity of the electrodes, and electrically connected to the control unit, the collector electrode cooperating with the electrodes to stimulate the skin receptors.

12. A device as claimed in claim 11, wherein the electrodes are cathodes, and the collector electrode is an anode.

13. A device as claimed in claim 12, wherein the control unit is designed to activate the electrodes consecutively at a frequency of about 1–300 Hz, a current intensity not exceeding about 6 mA, and a pulse duration of about 0.01–5 ms.

14. A device as claimed in claim 12, wherein the electrode plate has a surface area of 4–300 cm$^2$, and that 2–100 electrodes are fixed in the electrode plate.

15. A device as claimed in claim 12, wherein the electrode tip portion of each electrode is pointed, being formed with one of a cutting edge or so small a cross-sectional surface that the skin portion is penetrated, regardless of the design of the electrode tip, and the electrode tip portion is surrounded by the stop means at a distance of about 0.2–1.2 mm from the tip.

16. A device as claimed in claim 12, wherein the stop means has a contact surface with the skin that is flat closest to the electrode tip portion and rounded up toward the electrode plate.

17. A device as claimed in claim 12, comprising at least one electrode plate connected for stimulating a major skin portion.

18. A device as claimed in claim 12, wherein the stop means has a surface for contact with the skin that is conical, an angle between the electrode tip portion and the stop means not exceeding 160°.

19. A device as claimed in claim 1, wherein the stop means is shaped with a convex skin contact surface surrounding the electrode tip.

20. A device as claimed in claim 1, wherein the stop means is a cylindrical shaped element having a flat contact surface for contact with the skin to be stimulated.

21. A device as claimed in claim 1, wherein the stop means has a surface for contact with the skin that is conical, an angle between the electrode tip portion and the stop means not exceeding 160°.

22. A method for relieving chronic and acute states of pain as well as itch, for affecting the motor activity of disabled people, or for increasing the flow-through of blood in underlying tissue, comprising;

applying with pressure to a skin portion to be stimulated a device which comprises a shapable electrode plate through which extend a plurality of electrodes which are fixed in the electrode plate and terminate, at their respective free ends, in electrode tip portions for skin penetration, the electrode tip portion of each electrode being surrounded, at a distance of about 0.1–2.0 mm from the electrode tip, by a stop means separating the electrode plate from the skin portion, the electrodes cooperating with a collector electrode of opposite electrical polarity to the electrodes, and the electrodes and the collector electrode being electrically connected to a control unit designed to activate the electrodes consecutively;

the device being applied so that the electrode tip portions penetrate the isolating outer layers of the epidermis to stimulate the receptors of the skin; and activating the electrodes consecutively by the control unit at a frequency of about 1–300 Hz, a current intensity not exceeding about 6 mA and a pulse duration of about 0.01–5 ms during a stimulation period of up to about 1 hour.

23. The use of a device for relieving chronic and acute states of pain as well as itch, for affecting the motor activity of disabled people, or for increasing the flow-through of blood in underlying tissue, the device comprising a shapable electrode plate through which extend a plurality of electrodes fixed in the electrode plate and terminating, at their respective free ends, in electrode tip portions for Skin penetration, the electrode tip portion of each electrode being surrounded, at a distance of about 0.1–2.0 mm from the electrode tip, by a stop means separating the electrode plate from the skin portion, the electrodes being electrically connected to a control unit designed to activate the electrodes consecutively, comprising the steps of applying the device to a selected area Of the skin so that the electrode tip portions penetrate the isolating outer layers of the epidermis to stimulate the receptors of the skin, and activating the device to electrically stimulate the skin.

24. The use of a device for relieving chronic and acute states of pain as well as itch, for affecting the motor activity of disabled people, or for increasing the flow-through of blood in underlying tissue, the device comprising a shapable electrode plate through which .extend a plurality of electrodes fixed in the electrode plate and terminating, at their respective free ends, in electrode tip portions for skin penetration, the electrode tip portion of each electrode being surrounded, at a distance of about 0.1–2.0 mm from the electrode tip, by a stop means separating the electrode plate from the skin portion, the electrodes cooperating with a collector electrode of opposite electrical polarity to the electrodes, the electrodes acting as cathodes and the collector electrode acting as an anode, and the electrodes and the collector electrode being electrically connected to a control unit designed to activate the electrodes consecutively, comprising the steps of applying the device to the skin so that the electrode tip portions penetrate the isolating outer layers of the epidermis to stimulate the receptors of the skin; and activating the electrodes consecutively by the control unit to stimulate an area of the skin.

* * * * *